US 6,623,421 B1

(12) United States Patent
Rivero Rodriguez et al.

(10) Patent No.: US 6,623,421 B1
(45) Date of Patent: Sep. 23, 2003

(54) EXTERNAL MAGNETIC ACTUATION VALVE FOR INTRAURETHRAL ARTIFICIAL URINARY SPHINCTER

(75) Inventors: Guillermo Rivero Rodriguez, Las Rozas (ES); Marta Multigner Dominguez, Las Rozas (ES); Jose Maria Garcia Paez, Madrid (ES); Joaquin Carballido Rodriguez, Madrid (ES); Eduardo Jorge Herrero, Madrid (ES); Francisco Javier Tendillo Cortijo, Madrid (ES)

(73) Assignee: Universidad Complutense de Madrid, Madrid (ES)

( * ) Notice: Subject to any disclaimer, the term of this patent is extended or adjusted under 35 U.S.C. 154(b) by 0 days.

(21) Appl. No.: 09/673,162
(22) PCT Filed: Feb. 11, 2000
(86) PCT No.: PCT/ES00/00049
§ 371 (c)(1), (2), (4) Date: Jan. 11, 2001
(87) PCT Pub. No.: WO00/47141
PCT Pub. Date: Aug. 17, 2000

(30) Foreign Application Priority Data

Feb. 11, 1999 (ES) .............................................. 9900284

(51) Int. Cl.[7] .................................................. A61F 2/00
(52) U.S. Cl. ....................................................... 600/29
(58) Field of Search ............ 600/29–30; 128/DIG. 25; 604/9, 246, 247; 251/65, 337

(56) References Cited

U.S. PATENT DOCUMENTS

| 4,994,019 A | | 2/1991 | Fernandez et al. |
| 5,562,598 A | | 10/1996 | Whalen et al. |
| 6,066,088 A | * | 5/2000 | Davis .......................... 600/29 |

FOREIGN PATENT DOCUMENTS

| EP | 0182409 B1 | 5/1986 |
| EP | 0357846 B1 | 3/1990 |
| ES | 2025946 A6 | 4/1992 |
| FR | 2655536 A1 | 6/1991 |
| WO | WO 95/17862 | 7/1995 |
| WO | WO 95/29716 | 11/1995 |
| WO | WO 99/18885 | 4/1999 |
| WO | WO 99/51293 | 10/1999 |

* cited by examiner

*Primary Examiner*—John P. Lacyk
(74) *Attorney, Agent, or Firm*—Katten Muchin Zavis Rosenman

(57) ABSTRACT

External magnetically actuated valve for an artificial intraurethral urinary sphincter. External magnetically actuated valve for an artificial intraurethral urinary sphincter, allowing urine control for people suffering from urinary incontinence or retention, by the application of an external magnetic field. After valve (1), object of the present invention, is placed in the patient's urethra (9), said patient may control urination. Urine is evacuated when a permanent magnet (3) is approached to the body of the patient. Closing is automatic. The system is provided with a safety system to prevent over pressures in bladder (8).

9 Claims, 3 Drawing Sheets

EXTERNAL MAGNETIC ACTUATION VALVE FOR INTRAURETHRAL ARTIFICIAL URINARY SPHINCTER

OBJECT OF THE INVENTION

The present invention relates to a valve model for an artificial urinary sphincter to be placed intraurethrally in humans, which performs the functions of the external urinary sphincter, meant for treating urinary incontinence and/ or retention. Opening of said valve is controlled from outside the human body by the application of a magnetic field created by a permanent magnet. The valve is closed automatically by a permanent magnet placed inside the valve.

The purpose of the present invention is the recovery of self-control of urination for those people who have lost it by means of an easily implanted prosthesis.

BACKGROUND OF THE INVENTION

Hitherto, people suffering from urinary incontinence or retention deal with said problem with soakers, or probes provided with urine collection bags. The former is uncomfortable and causes serious social problems, while the latter often causes infections, often with a fatal outcome due to kidney failure. Work has been directed for some time towards designing prostheses which may replace the function of the urinary sphincter, although there is none yet in widespread use.

There exist some prosthesis which involve voluntary strangulation of the urethra (U.S. Pat. No. 3,744,063, U.S. Pat. No. 3,854,469, U.S. Pat. No. 3,903,849, EP0314258). The one used most has been commercialized under the name AMS-800 of American Medical System. Implantation of this type of prosthesis requires invasive surgery. Additionally, the firm Uroquest has developed a system to fight urinary incontinence consisting of a probe with an outlet orifice at the end of the urethra, but which does not reach the exterior and which is opened by means of an external magnet.

The device object of the present invention allows control of urination by the patient and may be implanted without need of surgery by cytoscopy.

SUMMARY OF THE INVENTION

The external magnetically actuated valve for an artificial intraurethral urinary sphincter is, in essence, a fluid cut-off valve with an attachment system similar to that used in urethral probes, which can be implanted by cytoscopy.

The valve is essentially comprised of:
- a hollow cylindrical body, made of a biocompatible material (e.g. Teflon), constituting the valve body, with an inlet sector and an outlet sector communicated by a central orifice, so that it can be crossed by a fluid.
- a piston that can slide inside the outlet sector of the cylindrical body, made of a soft magnetic material (e.g. Fe—Si 3%) and coated with a biocompatible material (e.g. Teflon). One of its ends has a cone or sphere shape to improve the seal of the central orifice.
- an internal permanent magnet (e.g. NdFeB), toroidal in shape and magnetically hard, coated with a biocompatible material (e.g. Teflon) disposed in the inlet sector of the cylindrical valve body.

The valve operation is as follows:

The internal permanent magnet exerts an attractive force on the internal piston until the conical or hemispherical end of the piston covers the central orifice of the cylindrical body, closing the valve. An external permanent magnet is used to open the valve. When said external permanent magnet is approximated from outside the person's body to the area where the valve is implanted it exerts a greater force on the piston than that exerted by the internal permanent magnet, in the opposite sense, due to the reorientation of the magnetic moment of the piston, opening the valve and allowing urine to exit. When the external permanent magnet is removed the force of the internal permanent magnet on the piston makes it close again the central orifice, cutting off the outwards flow of urine.

The valve is also provided with a safety system based on the fact that the force exerted by a magnet on a ferromagnetic object, the piston in this case, falls rapidly with the distance between them. More specifically, when the urine reaches a threshold pressure the piston is separated, so that the force exerted by the internal magnet on the piston falls and the piston will be displaced until the valve is fully opened. This allows ensuring that when it is not possible to apply an external magnetic field for any reason the pressure in the bladder will never exceed a certain value, preventing damage to the urinary system due to excess pressure in the bladder.

DETAILED DESCRIPTION OF THE INVENTION

Figure 1:
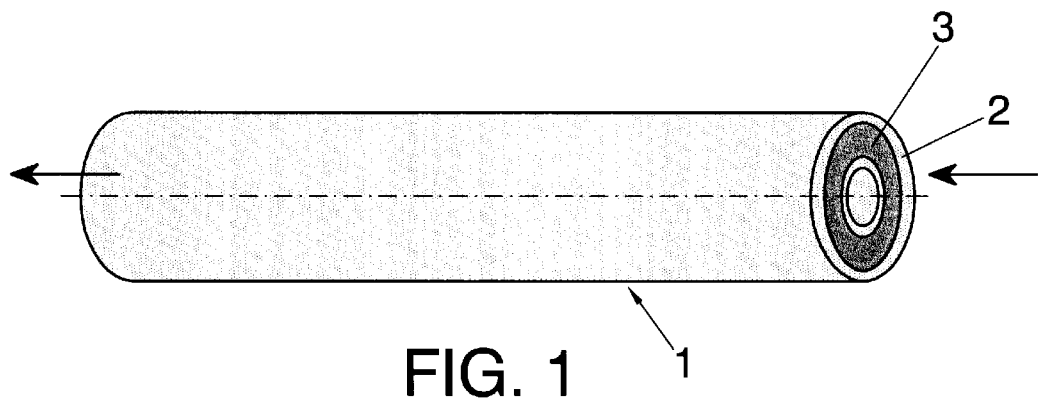
FIG. 1 shows a perspective view of the hollow cylindrical body with the internal permanent magnet housed inside it.
Figure 2:
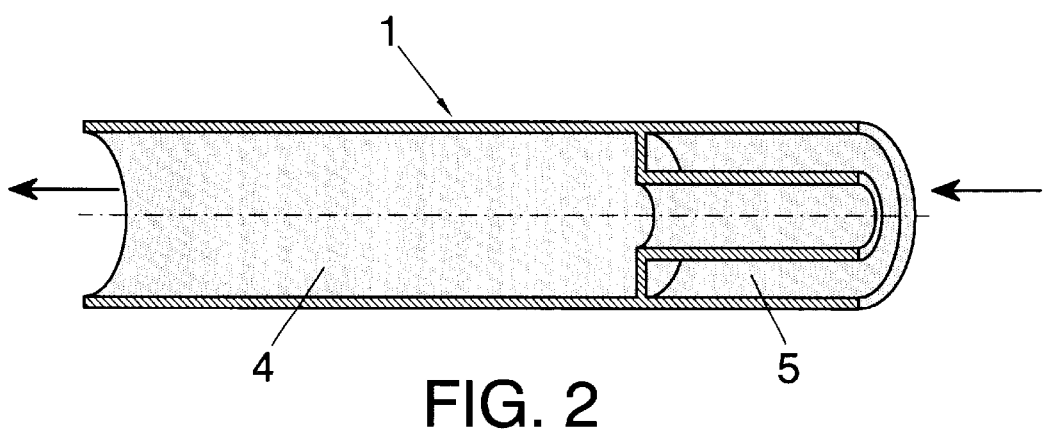
FIG. 2 shows a sectional view of the cylindrical body in a possible embodiment, incorporating an inner tubular segment in its inlet sector and a cylindrical conduct in its outer segment.
Figure 3:
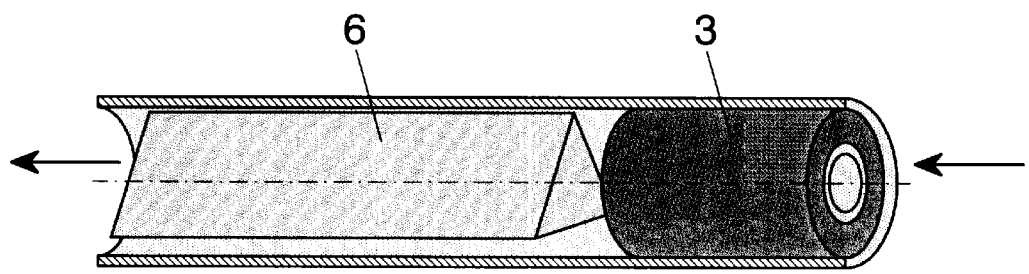
FIG. 3 shows a sectional view of the cylindrical body revealing a piston with a triangular section placed inside it and the internal permanent magnet.
Figure 4:
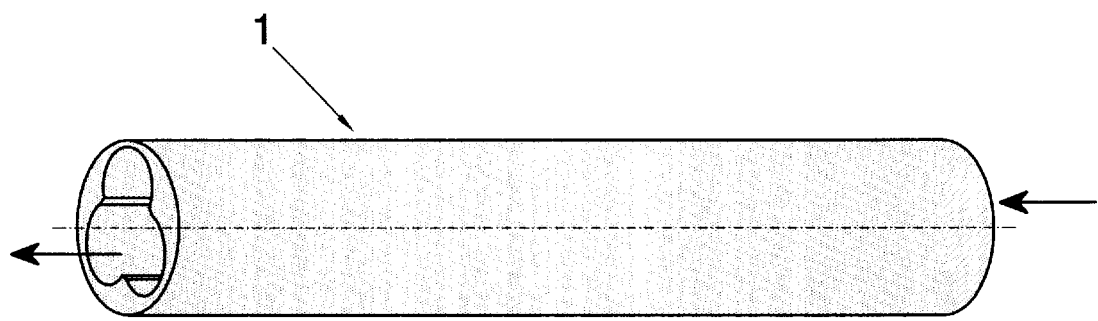
FIG. 4 shows an external view of the cylindrical body in another possible embodiment of the outlet sector revealing a conduct defined by three partially cylindrical portions offset 120° with each other.
Figure 5:
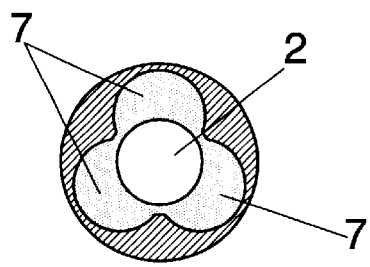
FIG. 5 shows a cross section through FIG. 4.
Figure 6:
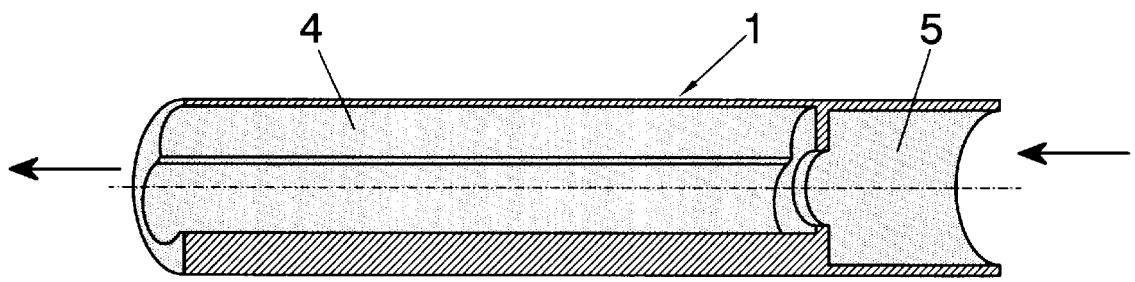
FIG. 6 shows a sectional view of the embodiment shown in FIG. 4, showing the inlet sector and the outlet sector separated by a wall.
Figure 7:
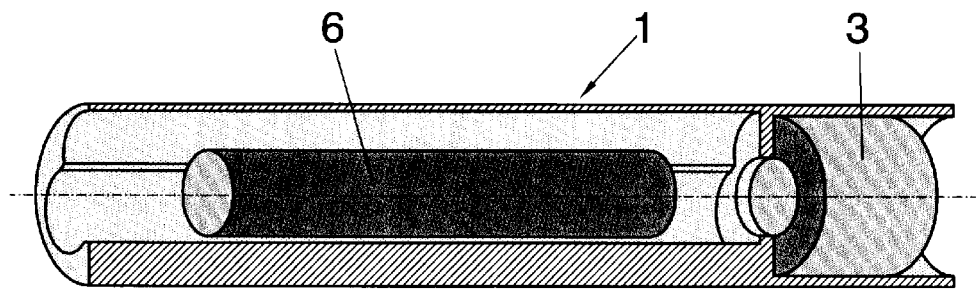
FIG. 7 shows a sectional view of the cylinder shown in FIG. 6 representing a piston with a circular section that moves centered within the conduct of the outlet sector defined by three partially cylindrical portions, as well as showing an internal permanent magnet housed in the inlet sector.

In view of the figures, it can be seen that the magnetically and externally actuated valve for an artificial intraurethral urinary sphincter housed in the urethra (9) comprises the following elements:
- a hollow cylindrical body (1), made of biocompatible material internally provided with a urine inlet sector (5) and a urine outlet sector (4) communicated by a central orifice (2), a piston (6), made of a magnetically soft ferromagnetic material coated in a biocompatible material that moves axially within the outlet sector (4) of the hollow cylindrical body (1) to open or close the central orifice (2), an internal permanent magnet (3) with a toroidal shape, magnetically hard, coated in a biocompatible material, placed in the inlet sector (5) of the hollow cylindrical body (1), exerting an attractive force on the piston (6), and an external permanent magnet (11) that when approximated to the valve from outside the human body exerts a force on the piston (6) that is greater than the attractive force of the internal permanent magnet (3) and opposite in sense, opening the central orifice (2) and allowing outlet of urine, while when the force of the external permanent magnet (11) on the piston (6) is removed, the piston (6) moves to automatically cover the central orifice (2) and close the urine passage.

Figure 8:
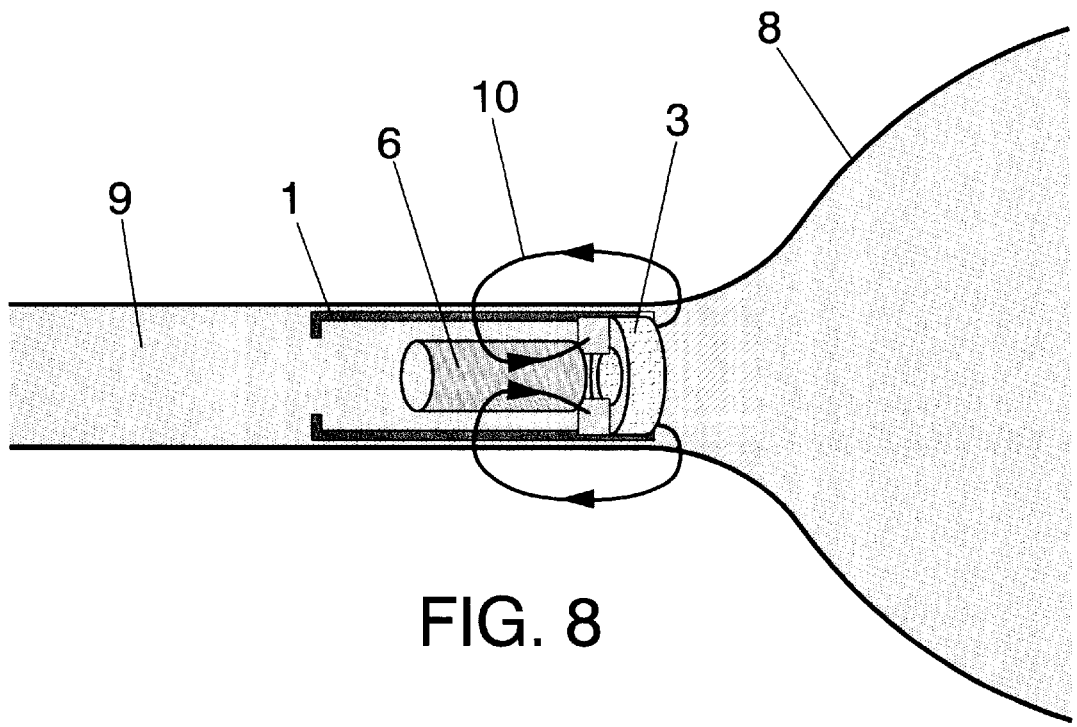
FIG. 8 shows the closed valve in the urethra with the piston being attracted by the internal permanent magnet.
Figure 9:
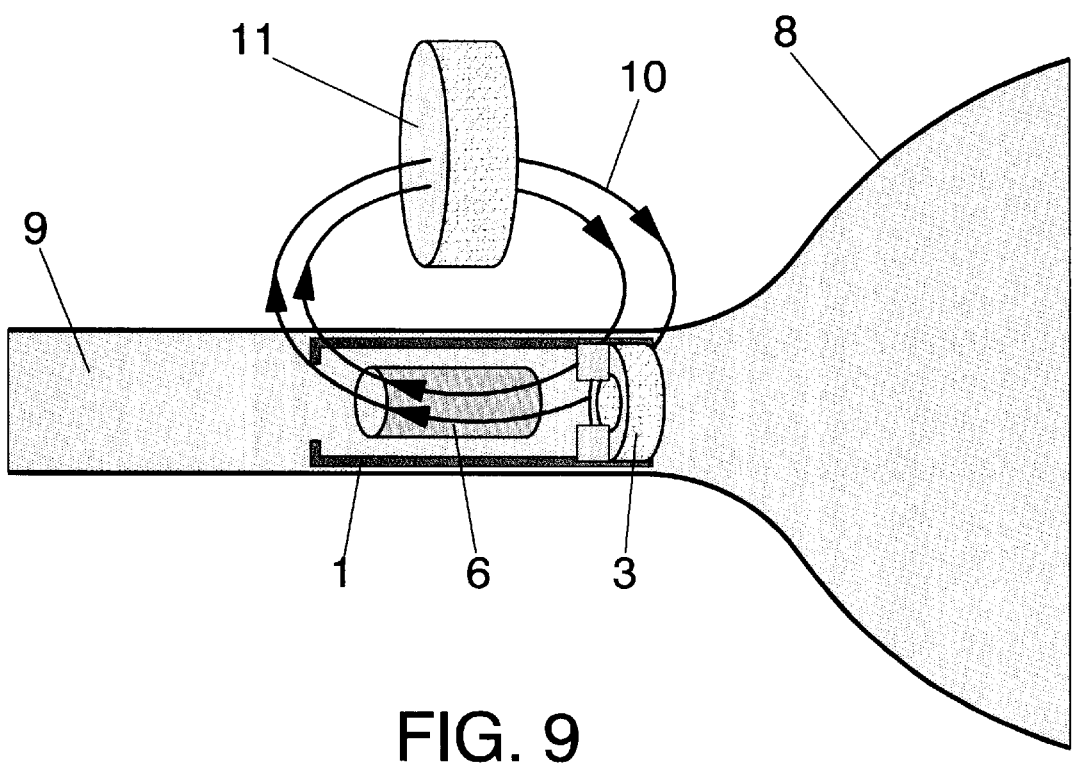
FIG. 9 shows the open valve in the urethra with the external magnet applying a magnet field that determines a separation of the piston from the internal magnet.

FIGS. 8 and 9 show the magnetic field lines (10) created by the internal magnet (3) and the external magnet (11) respectively.

The piston (6) can have a triangular or circular section, in both cases one of its ends being shaped as a hemisphere or as a cone oriented towards the central orifice (2) to improve its seal.

In a possible embodiment, the outlet sector (4) of the cylindrical body (1) has a cylindrical internal conduct in which moves the piston (6), and in another possible embodiment said sector (4) has a conduct defined by three partially cylindrical portions (7) offset 120° to each other, between which moves axially the piston (6).

Optionally, the cylindrical body (1) can incorporate in its inlet sector (5) a centered tubular portion (12) that rises from the central orifice (2) and on which the fixed permanent magnet (3) is coupled.

The central orifice (2) is defined in a wall separating the inlet sector (5) from the outlet sector (4), said wall having the same thickness as the separation between the piston (6) and the internal permanent magnet (3) in the closed position.

The attractive force between the internal permanent magnet (3) and the piston (6) is opposed by a force exerted by the pressure of urine contained in the bladder, which increases as more urine is retained until reaching a threshold value over which the piston (6) will be displaced; the attractive force exerted by the magnet (3) on the piston will fall as the distance between them increases, causing an automatic opening of the valve, thereby constituting a safety system that prevents damage to the urinary system due to excessive pressure in the bladder (8).

As the distance between the piston (6) and the internal magnet (3) increases, this is, the greater the thickness of the wall separating them, the lower the attractive force and thus the lower the threshold value over which the valve opens due to excessive pressure.

PREFERRED EMBODIMENT OF THE INVENTION

The present invention relates to an external magnetically actuated valve for an artificial intraurethral urinary sphincter and is illustrated by the following examples:

Six different prototypes of the device have been constructed. The soft magntic materials used were sweet Fe, Fe—Si and Fe—P. The hard magnetic materials were magnets of NdFeB, SmCo and AlNiCo. These prototypes were tested in vitro in a hydrodynamical facility in which the tight seal, functioning of the safety system, opening of the valve by applicaiton of an external magnetic field, evacuation flow and automatic closing were tested.

For in vivo tests two identical prototypes were constructed. A hollow cylindrical body which conforms the valve body was made in Teflon. Said body is provided with a cavity in the inlet orifice in which is placed the internal magnet under pressure. The permanent internal magnet is made of NdFeB and is coated in Teflon to avoid biologic incompatibilities. The pistons, which have a triangular base and a cone-shaped end are made of sweet Fe and coated in Teflon for the same reasons as above. The external permanent magnet is made of NdFeB.

The prototypes were inserted by urologist surgeons using surgical techniques in two pigs, one male and one female, in which a chronic urinary incontinence had been previously caused. Tight seal of the valve was tested to a pressure of 40 cm. $H_2O$. When the external magnet was placed near the valve, which was already in the animal's urethra the animal's urine was evacuated.

What is claimed is:

1. External magnetically actuated valve for an artificial intraurethral urinary sphincter, comprising:

a hollow cylindrical body made of biocompatible material and internally provided with a urine inlet sector and a urine outlet sector communicated by a central orifice, a piston made of a magnetically soft ferromagnetic material coated in a biocompatible material that moves axially within the urine outlet sector of the hollow cylindrical body to open or close the central orifice, an internal permanent magnet with a toroidal shape, magnetically hard, coated in a biocompatible material, placed in the urine inlet sector of the hollow cylindrical body, exerting an attractive force on the piston, and an external permanent magnet that when positioned in close proximity to the piston from outside the body exerts a force on the piston that is greater than the attractive force of the internal permanent magnet and opposite in sense, opening the central orifice and allowing outlet of urine, while when the force of the external permanent magnet on the piston is removed, the piston moves to automatically cover the central orifice and prevent the outlet of urine.

2. External magnetically actuated valve for an artificial intraurethral urinary sphincter according to claim 1, wherein the piston has a triangular cross-section.

3. External magnetically actuated valve for an artificial intraurethral urinary sphincter according to claim 1, wherein the piston has a circular cross-section.

4. External magnetically actuated valve for an artificial intraurethral urinary sphincter according to claim 1, wherein an end of the piston is shaped as a cone oriented towards the central orifice to improve its closure.

5. External magnetically actuated valve for an artificial intraurethral urinary sphincter according to claim 1, wherein an end of the piston is shaped as a hemisphere oriented towards the central orifice to improve its closure.

6. External magnetically actuated valve for an artificial intraurethral urinary sphincter according to claim 1, wherein the urine inlet sector incorporates a centered tubular portion on which is coupled the fixed permanent magnet.

7. External magnetically actuated valve for an artificial intraurethral urinary sphincter according to claim 1, wherein the urine outlet sector of the hollow cylindrical body has an internal cylindrical conduct.

8. External magnetically actuated valve for an artificial intraurethral urinary sphincter according to claim 1, wherein in which the outlet sector of the cylindrical body has a conduct defined by three partially cylindrical portions offset 120° to each other.

9. External magnetically actuated valve for an artificial intraurethral urinary sphincter according to claim 1, wherein the central orifice is provided with a wall separating the urine inlet sector from the urine outlet sector, said wall having the same thickness as a separation between the piston and the internal permanent magnet in the closed position, in which situation they are attracted by a force that is in turn opposed by a force exerted by the pressure of urine contained in the bladder, which force increases as more urine is retained until reaching a threshold value over which the piston will be displaced, the attractive force between the internal permanent magnet and the piston falling with the distance between them, causing an automatic opening of the valve, thereby constituting a safety system that prevents damage to the urinary system due to excessive pressure in the bladder.

* * * * *